(12) United States Patent
Ishii (10) Patent No.: US 8,765,696 B2
(45) Date of Patent: Jul. 1, 2014

(54) STEROID COMPOUND

(75) Inventor: Takayuki Ishii, Tokyo (JP)

(73) Assignee: Mikasa Seiyaku Co., Ltd., Tokyo (JP)

( * ) Notice: Subject to any disclaimer, the term of this patent is extended or adjusted under 35 U.S.C. 154(b) by 44 days.

(21) Appl. No.: 13/255,820

(22) PCT Filed: Mar. 8, 2010

(86) PCT No.: PCT/JP2010/054269
§ 371 (c)(1),
(2), (4) Date: Nov. 21, 2011

(87) PCT Pub. No.: WO2010/104187
PCT Pub. Date: Sep. 16, 2010

(65) Prior Publication Data
US 2012/0059158 A1     Mar. 8, 2012

(30) Foreign Application Priority Data
Mar. 9, 2009   (JP) ................. 2009-055172

(51) Int. Cl.
*A61K 31/70* (2006.01)
*C07H 15/24* (2006.01)

(52) U.S. Cl.
CPC ............................. *C07H 15/24* (2013.01)
USPC ................................................. 514/26; 536/5

(58) Field of Classification Search
USPC ................................................. 536/5; 514/26
See application file for complete search history.

(56) References Cited

U.S. PATENT DOCUMENTS

| 5,482,934 A | 1/1996 | Calatayud et al. |
| 5,733,901 A | 3/1998 | Gutterer |

FOREIGN PATENT DOCUMENTS

| GB | 1015396 | 0/1965 |
| WO | WO 93/22334 A1 | 11/1993 |
| WO | WO 95/09177 A1 | 4/1995 |
| WO | WO 99/47541 A1 | 9/1999 |
| WO | WO 99/47542 A1 | 9/1999 |
| WO | WO 2005/025577 A1 | 3/2005 |

OTHER PUBLICATIONS

International Search Report issued in PCT/JP2010/054269, mailed May 25, 2010.
Mutch, E.; "The role of esterases in the metabolism of ciclesonide to desisobutyryl-ciclesonide in human tissue," Biochemical Pharmacology 73(10); pp. 1657-1664; 2007.
Rizzo, M; "Inhaled corticosteroids in the treatment of respiratory allergy: safety vs. efficacy"; Jornal de Pediatria 2006; 82 (5 Suppl.); pp. S198-S205.
Cerasoli, F.; "Developing the ideal inhaled corticosteroid"; Chest, 2006, 130 (1 Suppl.); pp. 54S-64S.
J.Am. Chem. Soc. 1965, 86, pp. 3903-3904; FR3627 (1965).
Taiwanese Office Action issued Apr. 7, 2014.

*Primary Examiner* — Elli Peselev
(74) *Attorney, Agent, or Firm* — Greer Burns & Crain Ltd.

(57) ABSTRACT

A steroid compound of the Formula (1):

[wherein $R_1$ represents a group selected from the group consisting of H, $CH_3$, $C_2H_5$, $C_3H_7$ and $CH(CH_3)_2$, $R_2$ represents a group selected from $NH_2$, NHAc and $OCOR_1$, $R_3$ represents a group selected from the group consisting of $CH_3$, $COOCH_3$ and $CH_2OCOR_1$.]

10 Claims, 9 Drawing Sheets

STEROID COMPOUND

TECHNICAL FIELD

The present invention relates to steroid compounds. More particularly, the present invention relates to novel steroid compounds having an excellent pharmacological effect, which are produced by substituting the 21-position of des-ciclesonide with an acylated monosaccharide.

BACKGROUND ART

Prodrug steroid compounds which themselves do not have steroid-like activities but are converted to active compounds at the site of inflammation have been reported (Non-patent Literature 1, Patent Literature 1). However, although the compounds described in Non-patent Literature 1 and Patent Literature 1 have reduced side effects of steroid compounds, the reduction of side effects is insufficient. In view of this, a compound wherein hydroxyl groups of a simple sugar in a sugar-steroid compound are modified with bulky protective groups was synthesized, and release of steroid was suppressed at other than the site of inflammation, thereby attempting to reduce side effects (Technical Literature 2). Thereafter, compounds whose main effects are better separated from side effects by using as the steroid a metabolizable steroid was discovered (Patent Literature 3, Patent Literature 4).

PRIOR ART LITERATURES

Patent Literatures

Patent Literature 1 GB 1015396
Patent Literature 2 WO 95/09177
Patent Literature 3 WO 99/47541
Patent Literature 4 WO 99/47542

Non-Patent Literature

Non-patent Literature 1 J. Am. Chem. Soc. 1964, 86, 3903-4.

SUMMARY OF THE INVENTION

Object of the Invention

Although compounds whose actions are separated from side effects have been discovered by the above-described prior arts, the pharmacological effects of the steroids are smaller than known steroid drugs. The present inventors also evaluated the pharmacological effect of a compound prepared by adding, to budesonide, a sugar having a substitution with a bulky functional group, which evaluation was carried out using a dermatitis model by external administration, and it was confirmed that the pharmacological effect of the compound is smaller than that of a known steroid drug (budesonide). In the field of medicine, development of a steroid drug having a stronger activity while having less side effects is demanded.

An object of the present invention is to provide a steroid compound having a stronger anti-inflammatory action while having much less side effects.

SUMMARY OF THE INVENTION

The first aspect of the present invention is a steroid compound of the Formula (I).

[wherein $R_1$ represents a group selected from the group consisting of H, $CH_3$, $C_2H_5$, $C_3H_7$ and $CH(CH_3)_2$, $R_2$ represents a group selected from $NH_2$, NHAc and $OCOR_1$, $R_3$ represents a group selected from the group consisting of $CH_3$, $COOCH_3$ and $CH_2OCOR_1$]

The second aspect of the present invention is anti-inflammatory agents comprising as an effective ingredient a steroid compound of the Formula (I).

The third aspect of the present invention is dermatitis therapeutic agent comprising as an effective ingredient the compound of the Formula (I).

The 4th aspect of the present invention is asthma therapeutic agent comprising as an effective ingredient the compound of the Formula (I).

The 5th aspect of the present invention is rhinitis therapeutic agent comprising as an effective ingredient the compound of the Formula (I).

The 6th aspect of the present invention is arthritis therapeutic agent comprising as an effective ingredient the compound of the Formula (I).

The 7th aspect of the present invention is ulcerative colitis therapeutic agent comprising as an effective ingredient the compound of the Formula (I).

Effect of the Invention

The steroid compounds of the present invention have the advantageous feature that, by using des-ciclesonide as the steroid, a compound prepared by adding a sugar having a substitution with a non-bulky functional group unexpectedly has, upon external administration, a stronger anti-inflammatory effect than those of known steroid drugs while having much less systemic side effects. Further, the compounds of the present invention have the advantageous features that the glucosidase activity increases in the skin at the site of inflammation; the amount of release of sugar increases at site of inflammation; and the amount of steroid as the active main compound increases; while in normal skin, the glucosidase activity is low; the amount of production of the active compound is small; and hence side effects are less likely to occur. That is, the compounds of the present invention have the advantageous feature that not only systemic side effects but also local side effects are reduced.

In general, an ointment is applied to inflamed skin, but, since inflamed skin coexists with normal skin, the ointment is applied as a result not only to the inflamed skin but also to the normal skin. Of course, known steroid ointments have steroid activities also in normal skin, and this fact may lead to local side effects. On the other hand, it is thought that, since the compounds of the present invention show their anti-inflammatory effect after being changed to active compounds in inflamed skin and the amount of such change is small in normal skin, a strong action is not expressed in normal skin, which results in reduction of side effects.

BEST MODE FOR CARRYING OUT THE INVENTION

In the present specification, "des-ciclesonide" means an active metabolite of ciclesonide (Compound C in FIG. 1), which is used as an anti-asthmatic.

The present invention has a structure wherein a sugar is bound to the 21-position of des-ciclesonide, which sugar has a hydroxyl group protected with a protecting group. Examples of the sugar which is bound to the 21-position of des-ciclesonide include glucose, galactose, mannose, allose, altrose, gulose, idose, talose, glucosamine, galactosamine, mannosamine, N-acetylglucosamine, N-acetylgalactosamine and N-acetylmannosamine. These glycosides may be either α isomers or β isomers.

The compound of the present invention can be easily synthesized using a sugar as described above as a starting material, and typical examples of its reaction flow diagram are shown in FIGS. 1 to 9. For example, hydroxyl groups of the sugar as a starting material are protected with a toluoyl group(s) and/or an acetyl group(s), and the anomeric position is substituted with halogen, followed by reacting the resulting product with des-ciclesonide in the presence of a molecular sieve, and silver carbonate, silver triflate, silver perchlorate, or a Lewis acid such as tin tetrachloride, to obtain a compound of the present invention. In particular, in cases where the toluoyl group is employed as the protecting group, by-production of an ortho ester compound can be prevented, and the compound of interest can be efficiently obtained. Further, deprotection of the above compound can be easily carried out by deprotection using MeONa/MeOH, an aqueous sodium hydroxide solution or the like. The compound can be obtained also by acylation of the deprotected product.

Figure 1:
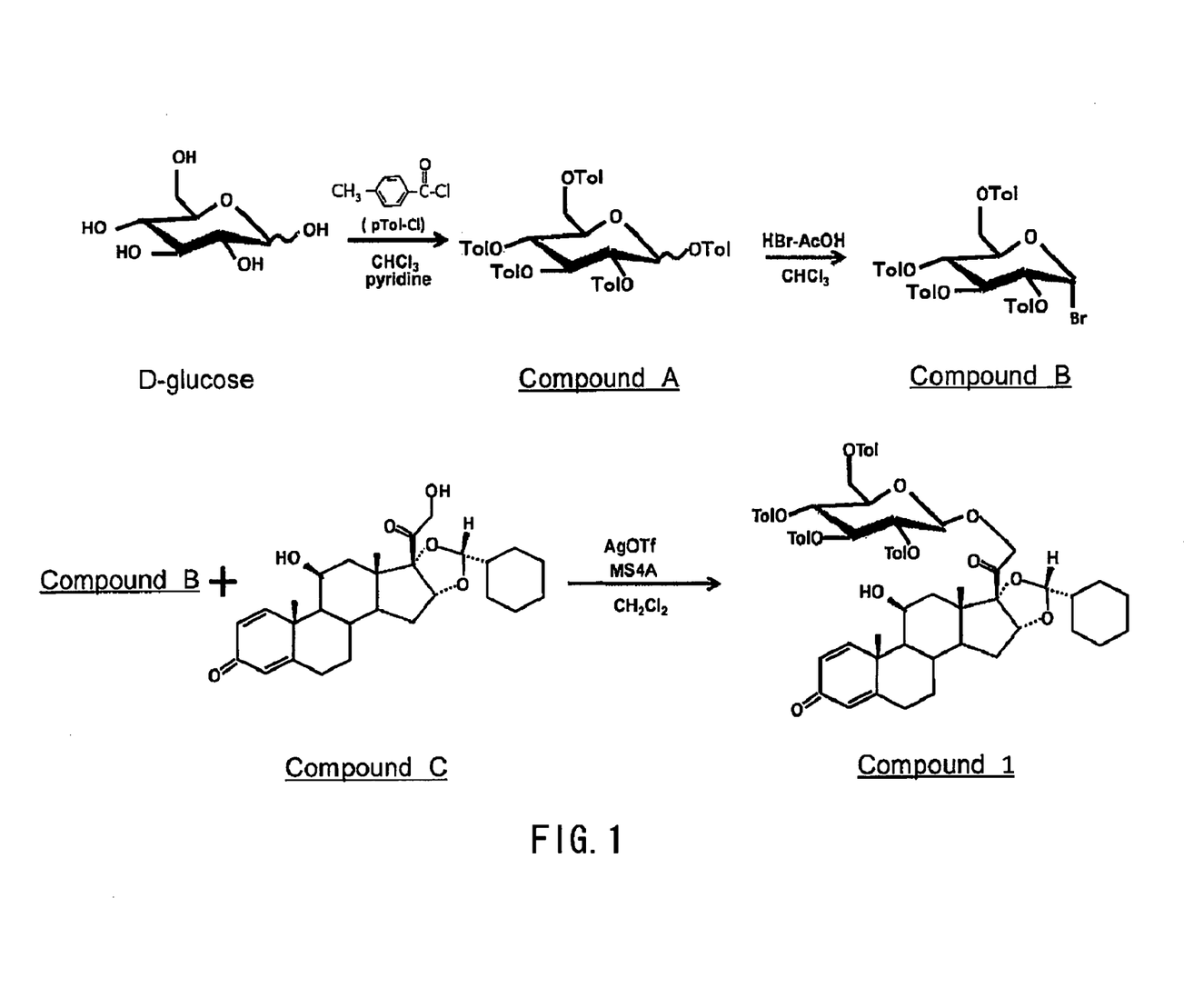
FIG. 1 is a reaction flow diagram for synthesis of D-glucose compound 1 (Example 1).
Figure 2:
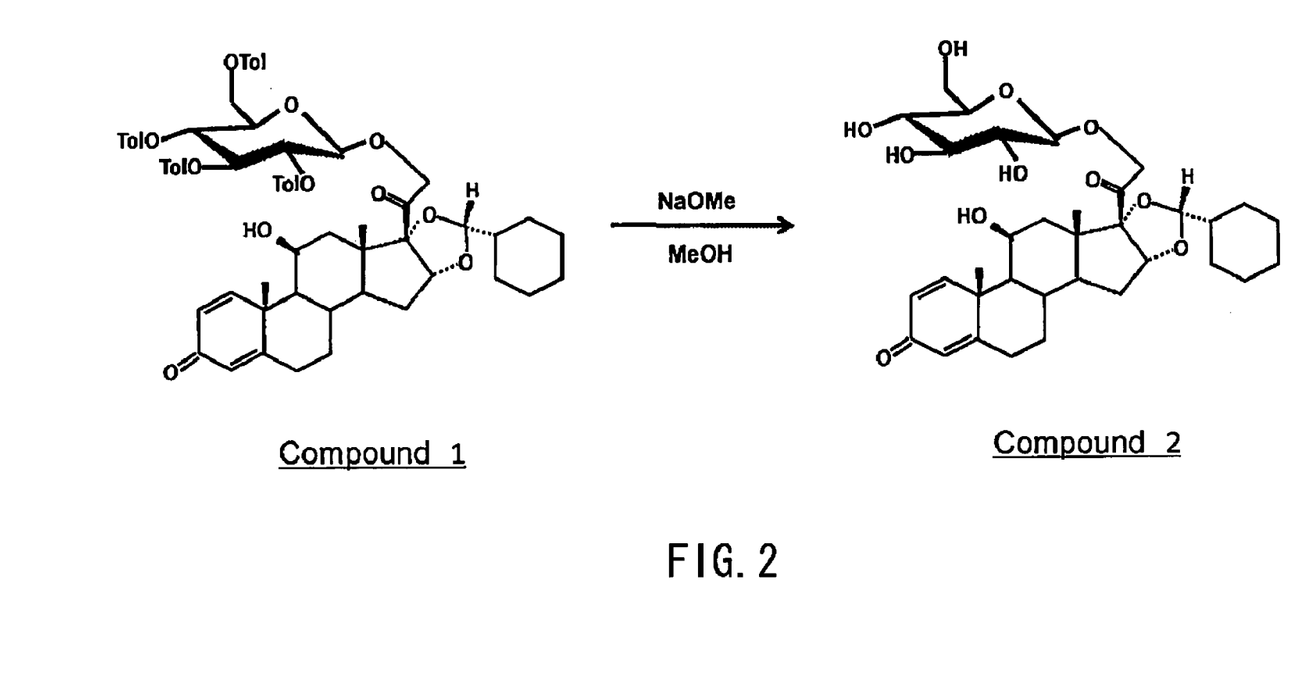
FIG. 2 is a reaction flow diagram for synthesis of Compound 2 from Compound 1 (Example 2).
Figure 3:
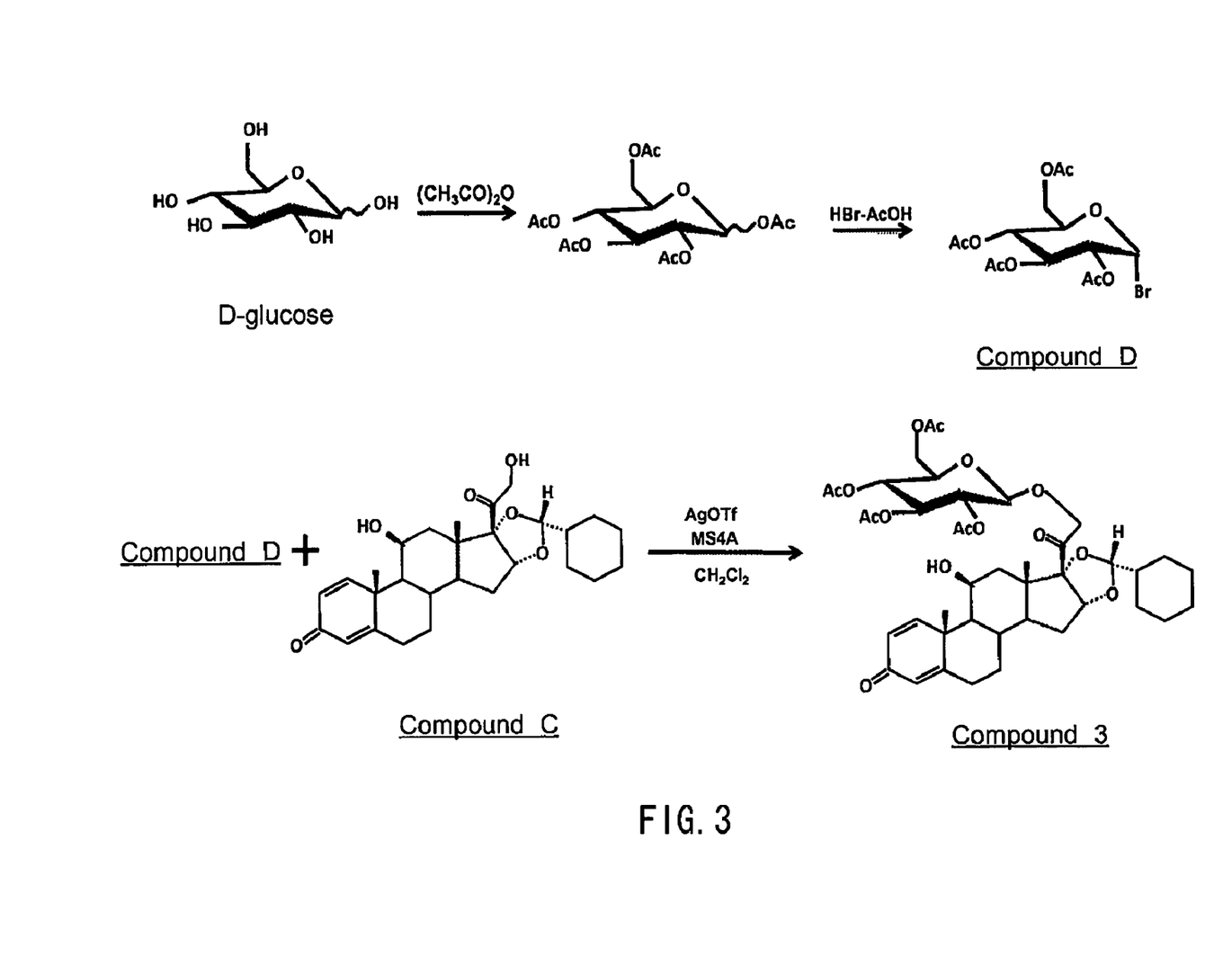
FIG. 3 is a reaction flow diagram for synthesis of Compound 3 from D-glucose (Example 3).
Figure 4:
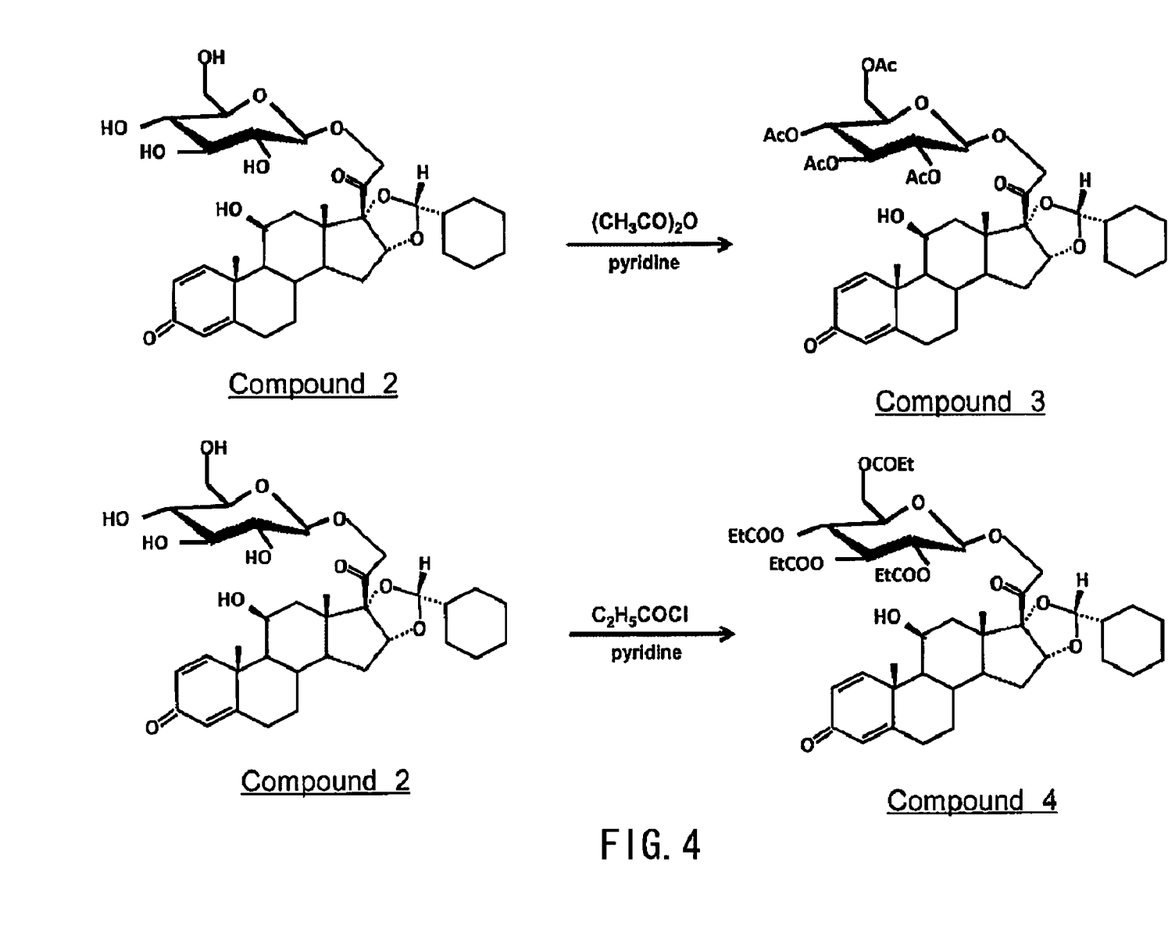
FIG. 4 is a reaction flow diagram for synthesis of Compound 3 and Compound 4 from Compound 2 (Example 4 and Example 5).

In particular, employment of the 5 steps from the reactions in FIG. 1 to the reaction in the top of FIG. 4 through the reaction in FIG. 2 is more preferred compared to employment of the 3 steps in FIG. 3 in view of the cost required for purification and in view of the yield.

Pharmaceuticals, especially anti-inflammatory agents, comprising as effective components compounds of the present invention may be used individually or in combination to prepare various formulations.

For eczema, dermatitides (including keratodermia tylodes palmaris progressiva, female facial melanosis, lichen simplex chronicus, radiodermatitis and solar dermatitis), cutaneous pruritus, prurigos (including lichen urticatus, strophulus and urticaria perstans), insect bites, psoriasis, pustulosis palmaris et plantaris, lichen planus, lichen nitidus, pityriasis rubra pilaris, pityriasis rosea Gibert, erythema group (including erythroderma due to malignant lymphoma), chronic discoid lupus erythematosus, drug eruption/toxicoderma, alopecia greata, burns (including cicatrices and keloids), chilblain, dermatitis herpetiformis Duhring (including pemphigoid), hemorrhoids and the like, a compound of the present invention may be used as an ointment, cream, lotion, tape, aerosol, solid ointment or the like for the skin or the like. Further, for otolaryngologic diseases such as allergic rhinitis, otitis externa, otitis media and surgical wounds including tympanoplasty/fenestration operation/radical operation of the inner ear, a compound of the present invention may be used as an intranasal inhalant, nasal drops, ear drops or the like. Further, for inflammatory diseases of the external eye, such as conjunctivitis, blepharitis and keratitis, a compound of the present invention may be used as eye drops or an eye ointment. Since the compounds of the present invention are less likely to cause systemic side effects, the drug concentration in the formulation may be increased, and the drug may be used as a 0.001% to 10.0% formulation, preferably 0.01% to 1.0% formulation, especially 0.05% to 0.5% formulation. Further, the compound may be used as a powder inhalant or aerosol inhalant for therapy of respiratory diseases such as bronchial asthma and COPD. Since the compounds of the present invention are less likely to cause systemic side effects, the drug concentration in the formulation may be increased, and the drug may be used as a formulation which may be applied in an amount of 1 μg to 1 mg, preferably 50 μg to 500 μg, especially 75 μg to 300 μg in terms of the amount for one time of spraying or inhalation. This formulation may be used either externally or as a therapeutic agent for arthritis to be intraarticularly administered or a therapeutic agent for ulcerative colitis to be orally administered.

The present invention will now be described by way of Examples.

Example 1

Synthesis of Compound 1 (FIG. 1)

Synthesis of Compound A: In 40 mL of chloroform, 1.2 g of D-(+)-glucose was dissolved, and 14.5 mL of p-toluoyl chloride and 8.9 mL of pyridine were added thereto at 0 to 5° C. The obtained mixture was stirred for 6 hours while slowly returning the temperature to room temperature. The reaction solution was poured into ice water and the resulting mixture was extracted with chloroform, followed by washing the organic layer with saturated copper sulfate solution, saturated aqueous sodium hydrogen carbonate solution and saturated brine. After drying the resultant over anhydrous magnesium sulfate, the solvent was evaporated under reduced pressure. An aliquot, in an amount of 5.33 g, of the obtained residue was subjected to separation and purification by silica gel column chromatography (toluene:ethyl acetate=50:1) to obtain 4.5 g of the Compound A as white powder.

$^1$H-NMR (CDCl$_3$) δ:2.309 (3H, s), 2.315 (3H, s), 2.362 (3H, s), 2.408 (3H, s), 2.474 (3H, s), 7.101 (2H, d, J=8.06), 7.106 (2H, d, J=8.06), 7.156 (2H, d, J=8.06), 7.207 (2H, d, J=8.06), 7.341 (2H, d, J=8.06), 7.775 (2H, d, J=8.06), 7.780 (2H, d, J=8.06), 7.834 (2H, d, J=8.06), 7.910 (2H, d, J=8.06), 8.062 (2H, d, J=8.06) MW=770.831

Synthesis of Compound B: In 20 mL of chloroform, 4.5 g of Compound A was dissolved, and 8.8 mL of hydrogen bromide solution in acetic acid was added thereto at 0 to 5° C., followed by stirring the mixture overnight while slowly returning the temperature to room temperature. After removing the unreacted bromine with argon gas, the solvent was evaporated under reduced pressure. The residue was dissolved in chloroform and the resulting mixture was washed with saturated aqueous sodium hydrogen carbonate solution. After drying the resultant over anhydrous magnesium sulfate, the solvent was evaporated under reduced pressure to obtain 2.5 g (59.2%) of Compound B as pale yellow powder.

$^1$H-NMR (CDCl$_3$) δ:2.299 (3H, s), 2.357 (3H, s), 2.365 (3H, s), 2.414 (3H, s), 6.849 (1H, d, J1=J2=4.03), 7.094 (2H, d, J=8.06), 7.160 (2H, d, J=8.06), 7.191 (2H, d, J=8.06), 7.236 (2H, d, J=8.06), 7.761 (2H, d, J=8.06), 7.830 (2H, d, J=8.06), 7.881 (2H, d, J=8.06), 7.944 (2H, d, J=8.06) MW=715.593

Synthesis of compound C: Methanol (51.6 mL) and tetrahydrofuran (25.8 mL) were added to ciclesonide (3.00 g) to dissolve the ciclesonide. While stirring the mixture, 5.55 mL of 1N NaOH was added. After continuing stirring for 30 minutes, amberlyst 15 was added to neutralize the mixture. After removing the amberlyst by filtration, the mixture was concentrated under reduced pressure, followed by purification by silica gel column chromatography to obtain Compound C (2.61 g, 100%).

$^1$H-NMR (CDCl$_3$) δ:0.92 (3H, s), 1.00-1.30 (8H, m), 1.45 (3H, s), 1.50-1.80 (10H, m), 2.02-2.21 (3H, m), 2.30-2.40 (1H, m), 2.52-2.62 (1H, m), 2.95-3.03 (1H, m), 4.20-4.30 (2H, m), 4.42-4.53 (2H, m), 4.88 (1H, d, J=4.7 Hz), 6.04 (1H, bs), 6.25-6.31 (1H, m), 7.24 (1H, d, J=10.1 Hz)

Synthesis of Compound 1: Compound B (1.462 g) and Compound C (600 mg) were dissolved in anhydrous dichloromethane (21 mL), and molecular sieves 4 Å (4.38 g) was added thereto. After stirring the mixture under an argon atmosphere at room temperature for 30 minutes, silver trifluoromethane sulfonate (492 mg) was added in an ice-salt bath, and the resulting mixture was stirred for 16 hours while slowly returning the temperature to room temperature, thereby carrying out the reaction. After adding saturated aqueous sodium hydrogen carbonate solution (30 mL) to the reaction solution and after stirring, the obtained mixture was extracted twice with chloroform (20 mL). After washing with saturated brine (20 mL), the chloroform layer was dried over anhydrous magnesium sulfate, and the solvent was evaporated under reduced pressure. The residue was subjected to separation and purification by silica gel column chromatography (sequentially eluted with n-hexane-ethyl acetate=3:1, 2:1, 1:1) to obtain 830 mg (58.9%) of Compound 1 as white powder. Simultaneously, 249 mg (41.5%) of Compound B was recovered.

Rf=0.28 (n-hexane-ethyl acetate=2:1)

$^1$H NMR (CDCl3, 500 MHz) δ:0.960 (3H, s, 18-CH$_3$), 1.494 (3H, s, 19-CH$_3$), 6.04 (1H, d, J=2.0 Hz, H4), 6.31 (1H, dd, J=2.0, 10.0 Hz, H2), 7.28 (1H, d, J=10.0 Hz, H1). glucose residue: 2.29, 2.35, 2.36, 2.41 (each 3H, s, CH$_3$C$_6$H$_5$COO× 4), 4.00 (1H, ddd, J=3.4, 4.1, 9.7 Hz, H5), 4.51 (1H, dd, J=3.4, 12.0 Hz, H6a), 4.79 (1H, dd, J=4.1, 12.0 Hz, H6b), 5.18 (1H, d, J=7.9 Hz, H1), 5.49 (1H, t, 9.7 Hz, H2), 5.70 (1H, t, J=9.7 Hz, H3), 5.87 (1H, t, 9.7 Hz, H4).

FAB-MS1105 (M+H)$^+$.

Example 2

Synthesis of Compound 2 (FIG. 2)

Compound 1 (887 mg) was dissolved in anhydrous methanol (10 mL) and anhydrous chloroform (5 mL), and 28% sodium methoxide (1 mL) was added dropwise thereto under an argon atmosphere at room temperature. The resulting mixture was stirred for additional 1 hour thereby carrying out the reaction. To this reaction solution, Dowex50W (H$^+$) which was strongly acid cation-exchange resin was added with stirring to neutralize the reaction solution. The mixture was subjected to suction filtration. After washing the obtained solution with methanol, the filtrate was evaporated under reduced pressure. The residue was subjected to purification by silica gel column chromatography (chloroform:methanol=10:1) to obtain 433 mg (85.3%) of Compound 2 as white powder.

Rf=0.36 (chloroform:methanol=5:1)

$^1$HNMR (CD$_3$OD) δ:0.94 (3H, s), 0.96-1.32 (8H, m), 1.49 (3H, s), 1.50-1.80 (9H, m), 1.80-2.00 (2H, m), 2.07-2.30 (2H, m), 2.32-2.43 (1H, m), 2.57-2.72 (1H, m), 3.21-3.40 (4H, m), 3.62-3.71 (1H, m), 3.84-3.92 (1H, m), 4.32 (1H, d, J=7.8 Hz), 4.36 (1H, d, J=4.2 Hz), 4.54 (1H, d, J=18.9 Hz), 4.76 (1H, d, J=18.9 Hz), 4.84 (1H, d, J=4.5 Hz), 6.01 (1H, br), 6.25 (1H, dd, J=10.0 Hz), 7.45 (1H, d, J=10.0 Hz) FAB-MS633 (M+H)$^+$.

Example 3

Synthesis of Compound 3 (FIG. 3)

Synthesis of Compound D: D-(+)-glucose (2.02 g), acetic anhydride (10 mL), 33 wt % hydrogen bromide/acetic acid (2 mL) was stirred overnight at room temperature in the dark, and 33 wt % hydrogen bromide/acetic acid (10 mL) was added thereto. After stirring the mixture for 7 hours, dichloromethane (50 mL) was added to the reaction solution. The resultant mixture was added to iced water (50 mL) and separated into aqueous layer and dichloromethane. The aqueous layer was extracted with dichloromethane (50 mL×2), followed by combining dichloromethane layer. The resulting solution was neutralized with sodium hydrogen carbonate solution, washed with water and brine, dried over MgSO$_4$, and concentrated under reduced pressure. Diisopropylether (6.5 g) was added to the concentrated residue (4.74 g) and added separately synthesized compound D thereto. Solidified masses were crushed and filtered, followed by washing with diisopropylether and drying under reduced pressure at room temperature, to obtain compound D (3.83 g, 83.1%).

Rf=0.45 (hexane:ethyl acetate=3:2)

$^1$H-NMR (CDCl$_3$) δ:2.04 (3H, s), 2.05 (3H, s), 2.098 (3H, s), 2.103 (3H, s), 4.09-4.17 (1H, m), 4.26-4.37 (2H, m), 4.84 (1H, dd, J=4.2, 9.9 Hz), 5.10-5.21 (1H, m), 5.56 (1H, dd, J=9.6, 9.6 Hz), 6.61 (1H, d, J=4.2 Hz)

Synthesis of Compound 3: Under an argon atmosphere, compound B (1.50 g), silver trifluoromethanesulfonate (0.908 g), molecular sieves 4 Å (3.60 g) and dichloromethane (25 mL) was stirred at room temperature for 3 hours in the dark. The reaction solution was cooled in ice water, the solution of compound 1 (1.31 g) in dichloromethane (15 mL) was added dropwise thereto at about 5° C. After stirring the resulting mixture for about an hour, the ice water bath was removed and the mixture was stirred at room temperature overnight. The reaction solution was filtered, and saturated aqueous sodium hydrogen carbonate solution (30 mL) was added thereto, followed by vigorously stirring the resulting mixture for 2.5 hours. The solution was separated, the dichloromethane layer was washed with brine and dried over $MgSO_4$, and the resulting solution was concentrated under reduced pressure. The concentrated residue (2.47 g) was subjected to purification by silica gel column chromatography to obtain 1.37 g (53.7%) of compound 3 as white powder.

Rf=0.11 (hexane:ethyl acetate=3:2)

$^1$H-NMR (CDCl$_3$) δ:0.90 (3H, s), 0.95-1.30 (7H, m), 1.47 (3H, s), 1.48-1.83 (9H, m), 1.96-2.21 (4H, m), 2.02 (3H, s), 2.04 (3H, s), 2.10 (3H, s), 2.12 (3H, s), 2.29-2.39 (1H, m), 2.50-2.65 (1H, m), 2.78 (1H, br), 3.64 (1H, ddd, J=9.9, 3.6, 3.6 Hz), 4.22 (1H, dd, J=12.2, 3.6 Hz), 4.26 (1H, d, J=4.8 Hz), 4.37 (1H, dd, J=12.2, 3.6 Hz), 4.51 (1H, d, J=18.9 Hz), 4.51 (1H, br), 4.59 (1H, d, J=18.9 Hz), 4.84 (1H, d, J=8.0 Hz), 4.87 (1H, d, J=4.8 Hz), 5.02 (1H, dd, J=9.3, 8.0 Hz), 5.11 (1H, dd, J=9.3, 9.3 Hz), 5.24 (1H, dd, J=9.3, 9.3 Hz), 6.03 (1H, br), 6.29 (1H, dd, J=10.2, 2.0 Hz), 7.30 (1H, d, J=10.2 Hz)

MS ESI (+) 823 (M+Na)$^+$.

Example 4

Synthesis of Compound 3 (FIG. 4)

Compound 2 (0.100 g) was dissolved in dry pyridine (10 mL), anhydrous acetic acid (1 mL) was added dropwise thereto while cooling in an ice water. After stirring at 5° C. for 18 hours, methanol was poured into the reaction solution, and then the mixture was stirred for 30 minutes. After concentrating the mixture under reduced pressure, the concentrated residue was subjected to purification by silica gel column chromatography to obtain 0.120 g (95%) of compound 3 as white powder.

Rf=0.11 (hexane:ethyl acetate=3:2)

Example 5

Synthesis of Compound 4 (FIG. 4)

Compound 2 (0.422 g) was dissolved in dry pyridine (21 mL), propionylchloride (0.550 mL) was added dropwise thereto while cooling in an ice water. The ice water bath was removed and after stirring at room temperature for 4 hours, the reaction solution was poured into ice water (60 g), the resulting mixture was extracted with ethyl acetate (50 mL). The ethyl acetate layer was washed with water, copper sulfate solution, water, saturated aqueous sodium hydrogen carbonate solution and brine, and dried over $MgSO_4$, followed by concentrating the mixture under reduced pressure. The concentrated residue (0.556 g) was subjected to purification by silica gel column chromatography to obtain 0.290 g (50.7%) of compound 4 as slightly yellow powder.

Rf=0.87 (chloroform:methanol=10:1)

$^1$H-NMR (CDCl$_3$) δ:0.90 (3E, s), 0.99-1.32 (20H, m), 1.47 (3H, s), 1.50-1.78 (8H, m), 1.95-2.22 (3H, m), 2.22-2.44 (9H, m), 2.52-2.62 (1H, m), 2.83-2.88 (1H, m), 3.58-3.65 (1H, m), 4.21-4.28 (3H, m), 4.36 (1H, dd, J1=12.1 Hz, J2=3.6 Hz), 4.47-4.63 (3H, m), 4.82-4.88 (2H, m), 5.04 (1H, dd, J1=9.5 Hz, J2=8.0 Hz), 5.13 (1H, dd, J1=J2=9.8 Hz), 5.27 (1H, dd, J1=J2=9.5 Hz), 6.03 (1H, bt), 6.29 (1H, dd, J1=10.1 Hz, J2=1.8 Hz), 7.30 (1H, d, J=10.1 Hz)

MS ESI (+) 879 (M+Na)$^+$.

Example 6

Figure 5:
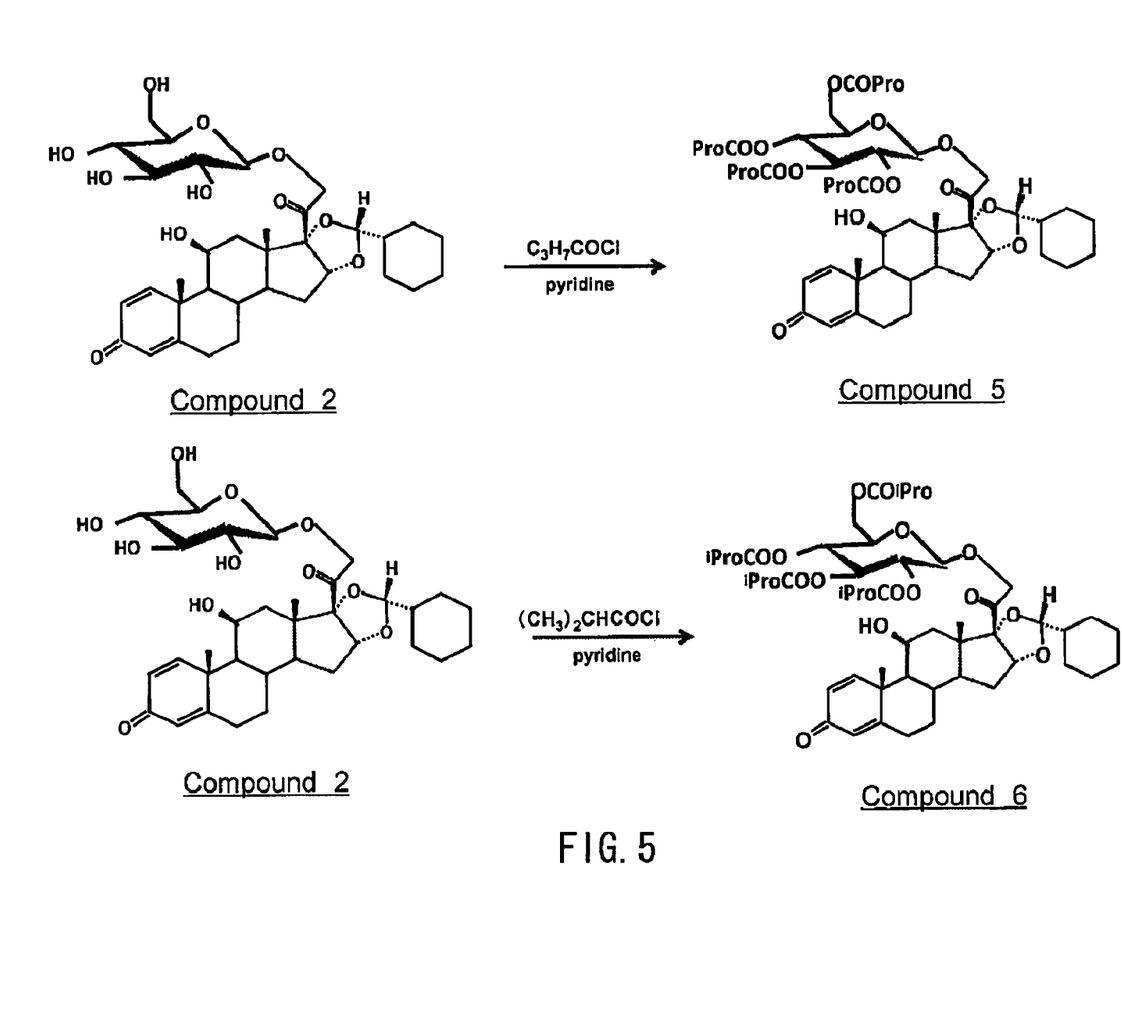
FIG. 5 is a reaction flow diagram explaining synthesis of Compound 5 and Compound 6 from Compound 2 (Example 6 and Example 7).

Synthesis of Compound 5 (FIG. 5)

Compound 2 (0.450 g) was dissolved in dry pyridine (20 mL), n-butyryl chloride (0.630 mL) was added dropwise thereto while cooling in an ice water. The ice water bath was removed and after stirring at room temperature for 4 hours, the reaction solution was poured into ice water (60 g), the resulting mixture was extracted with ethyl acetate (50 mL). The ethyl acetate layer was washed with water, copper sulfate solution, water, saturated aqueous sodium hydrogen carbonate solution and brine, and dried over $MgSO_4$, followed by concentrating the solvent under reduced pressure. The concentrated residue was subjected to purification by silica gel column chromatography to obtain 0.320 g (49.3%) of compound 5 as white powder.

$^1$H-NMR (CDCl$_3$) δ:0.80-1.30 (23H, m), 1.47 (3H, s), 1.48-1.80 (16H, m), 1.94-2.18 (3H, m), 2.18-2.42 (9H, m), 2.52-2.62 (1H, m), 2.88-2.33 (1H, m), 3.55-3.65 (1H, m), 4.19 (1H, dd, J1=12.1 Hz, J2=3.4 Hz), 4.25 (1H, d, J=4.5 Hz), 4.39 (1H, dd, J1=12.1 Hz, J2=3.5 Hz), 4.47-4.63 (3H, m), 4.82-4.88 (2H, m), 5.03 (1H, dd, J1=9.5 Hz, J2=8.0 Hz), 5.14 (1H, dd, J1=J2=9.8 Hz), 5.27 (1H, dd, J1=J2=9.5 Hz), 6.03 (1H, bt), 6.29 (1H, dd, J1=10.1 Hz, J2=1.8 Hz), 7.30 (1H, dd, J=10.1 Hz)

MS ESI (+) 935 (M+Na)$^+$.

Example 7

Synthesis of Compound 6 (FIG. 5)

Compound 2 (0.350 g) was dissolved in dry pyridine (16 mL), isobutylchloride (0.500 mL) was added dropwise thereto while cooling in an ice water. The ice water bath was removed and after stirring at room temperature for 4 hours, the reaction solution was poured into ice water (60 g), the resulting mixture was extracted with ethyl acetate (50 mL). The ethyl acetate layer was washed with water, copper sulfate solution, water, saturated aqueous sodium hydrogen carbonate solution and brine, and dried over $MgSO_4$, followed by concentrating the solvent under reduced pressure. The concentrated residue was subjected to purification by silica gel column chromatography to obtain 0.420 g (83.2%) of compound 6 as white solids.

$^1$H-NMR (CDCl$_3$) δ:0.90 (3H, s), 1.00-1.27 (32H, m), 1.47 (3H, s), 1.49-1.82 (8H, m), 1.95-2.22 (3H, m), 2.31-2.37 (1H, m), 2.44-2.66 (5H, m), 2.92-2.95 (1H, m), 3.55-3.62 (1H, m), 4.17 (1H, dd, J1=12.2 Hz, J2=3.0 Hz), 4.25 (1H, d, J=4.4 Hz), 4.40 (1H, dd, J1=12.2 Hz, J2=3.6 Hz), 4.45-4.62 (3H, m), 4.84-4.90 (2H, m), 5.03 (1H, dd, J1=8.0 Hz, J2=9.5 Hz), 5.12 (1H, dd, J1=J2=9.7 Hz), 5.31 (1H, dd, J1=J2=9.5 Hz), 6.03 (1H, bs), 6.27-6.31 (1H, m), 7.30 (1H, d, J=10.0 Hz)

MS ESI (+) 935 (M+Na)$^+$.

Example 8

Figure 6:
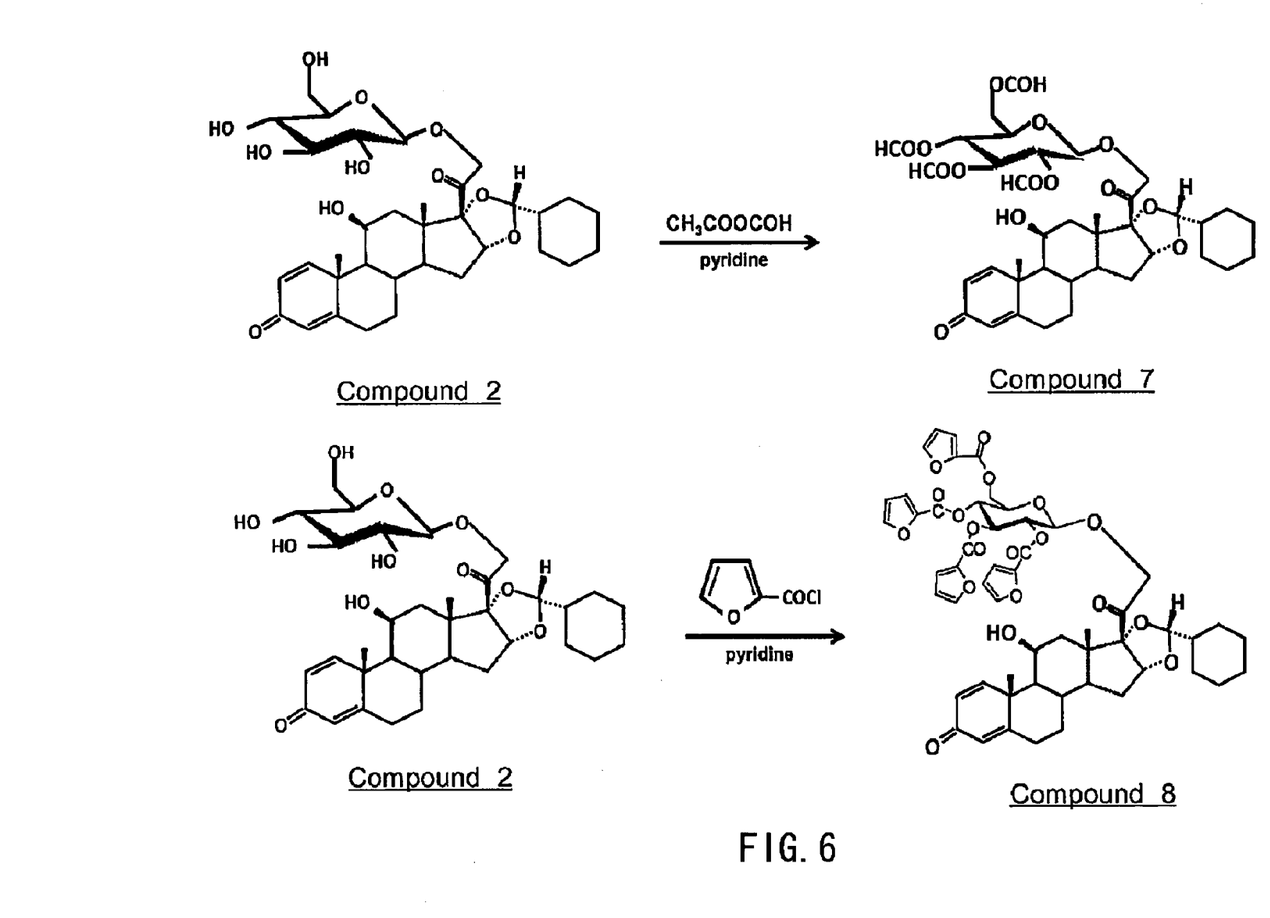
FIG. 6 is a reaction flow diagram explaining synthesis of Compound 7 and Compound 8 from Compound 2 (Example 8).

Synthesis of Compound 7 (FIG. 6)

Compound 2 (91 mg) was dissolved in dry pyridine (4 mL), while stirring the mixture, acetic acid formic acid anhydride (0.65 mL) was added dropwise dividedly in three times thereto at 5 to 10° C. in water bath. After stirring at room temperature for 20 hours, the reaction solution was poured into ice water (200 mL). The precipitated white solids were filtered with suction and after washing with water, dissolved by chloroform, dried over anhydrous magnesium sulfate.

Chloroform was removed under reduced pressure and the residue was subjected to purification by silica gel column chromatography (n-hexane-ethyl acetate=1:1) and the compound in which the glucose hydroxyl groups are partly substituted with acetyl groups was removed by using ODS column to perform preparative HPLC (methanol:water=75:25) to obtain 48 mg (45%) of compound 7 as white powder Rf=0.66 (n-hexane:ethyl acetate=1:1)

HPLC (ODS column, methanol-water=77:33, 1 mL/min, UV254 nm) Rt=12.07 min.

$^1$H NMR (CDCl$_3$) δ:0.90 (3H, s, 18-CH$_3$), 1.46 (3H, s, 19-CH$_3$), 6.03 (1H, d, J=1.8 Hz, H4), 6.29 (1H, dd, J=1.8, 10.0 Hz, H2), 7.28 (1H, d, J=10.0 Hz, H1). glucose residue: 3.75 (1H, ddd, J=3.1, 4.0, 10.0 Hz, H5), 4.22 (1H, dd, J=4.0, 12.0 Hz, H6a), 4.58 (1H, dd, J=3.1, 12.0 Hz, H6b), 4.99 (1H, d, J=7.8 Hz, H1), 5.15 (1H, t, J=8.1, 9.8 Hz, H2), 5.30 (1H, t, J=9.8, 10.0 Hz, H4), 5.50 (1H, t, J=9.5 Hz, H3), 8.05, 8.07, 8.10, 8.14 (each 1H, s, OCHO×4).

FAB-MS 745 (M+H)$^+$.

Example 9

Synthesis of Compound 8 (FIG. 6)

Compound 2 (0.473 g) was dissolved in dry pyridine (21.7 mL), 2-furoyl chloride (0.718 mL) was added dropwise thereto while cooling in an ice water. The ice water bath was removed and after stirring at room temperature for 3 hours, the reaction was stopped by adding water. The mixture was extracted with chloroform, washed with saturated aqueous sodium hydrogen carbonate solution and brine, dried over MgSO$_4$, and then the resultant was concentrated under reduced pressure. The concentrated residue was subjected to purification by silica gel column chromatography to obtain 0.708 g (94.0%) of compound 8 as white powder.

$^1$H-NMR (CDCl$_3$) δ:0.94 (3H, s), 0.96-1.27 (8H, m), 1.50 (3H, s) 1.52-1.78 (9H, m), 1.78-1.86 (1H, m), 1.94-2.23 (3H, m), 2.31-2.38 (1H, m), 2.53-2.63 (1H, m), 3.03-3.07 (1H, m), 3.95-4.01 (1H, m), 4.24 (1H, d, J=4.5 Hz), 4.42-4.58 (3H, m), 4.69 (1H, d, J=18.7 Hz), 4.75-4.86 (2H, m), 5.15 (1H, d, J=8.0 Hz), 5.39 (1H, dd, J1=8.0 Hz, J2=9.5 Hz), 5.60 (1H, dd, J1=J2=9.7 Hz), 5.74 (1H, dd, J1=J2=9.7 Hz), 6.04 (1H, bs), 6.28-6.33 (1H, m), 6.40-6.43 (1H, m), 6.45-6.49 (2H, m), 6.53-6.56 (1H, m), 7.12-7.18 (2H, m), 7.22-7.29 (2H, m), 7.37 (1H, d, J=10.1 Hz), 7.48-7.51 (1H, m), 7.53-7.57 (2H, m), 7.59-7.62 (1H, m)

Example 10

Figure 7:
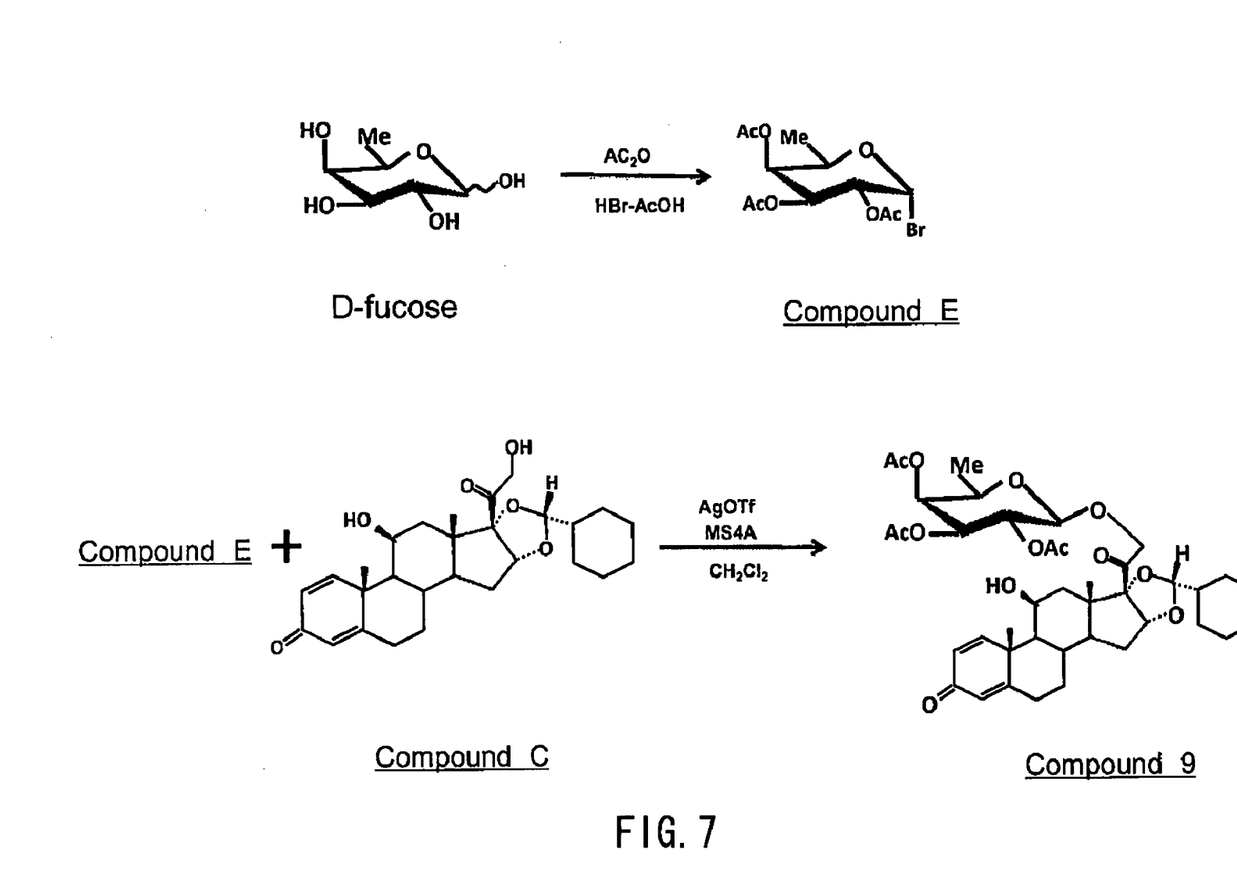
FIG. 7 is a reaction flow diagram for synthesis of Compound 9 from D-fucose (Example 9).

Synthesis of Compound 9 (FIG. 7)

Synthesis of Compound E: D-fucose (0.36 g) was dissolved in anhydrous acetic acid (1.97 mL), and 33 wt % of hydrogen bromide acetic acid solution (0.39 mL) was added thereto, followed by stirring the mixture overnight in the dark. 33 wt % of hydrogen bromide acetic acid solution (1.97 mL) was again added to the mixture. After stirring for 7 hours, dichloromethane (9.85 mL) was added thereto and the obtained solution was added to ice water (9.85 mL). After separation, the aqueous layer was extracted with dichloromethane. The resulting mixture was washed with saturated sodium hydrogen carbonate solution and after washing with water, dried over anhydrous sodium sulfate. After filtration, the resultant was concentrated under reduced pressure to obtain compound E (885 mg).

Synthesis of Compound 9: Under an argon atmosphere, compound C (1 g) was dissolved in dichloromethane (19.5 mL) in the dark, and silver trifluoromethanesulfonate (711 mg) and molecular sieves 4 Å (2.82 g) was added thereto, followed by stirring the mixture for 10 minutes. A solution of compound F (885 mg) in dichloromethane (11.7 mL) were added, and the mixture was heated to room temperature under stirring for 2 hours. After filtering the mixture, saturated sodium hydrogen carbonate solution was added thereto and after stirring, the mixture was separated. The solution was washed with saturated brine and dried over anhydrous sodium sulfate. After filtering, the obtained solution was concentrated under reduced pressure, the residue was subjected to purification by silica gel column to obtain 111 mg (28%) of compound 9 as white powder.

$^1$H-NMR (CDCl$_3$) δ:0.91 (3H, s), 0.98-1.30 (8H, m), 1.24 (3H, d, J=6.4 Hz), 1.45 (3H, s), 1.49-1.80 (10H, m), 2.00 (3H, s), 2.03-2.17 (3H, m), 2.13 (3H, s), 2.18 (3H, s), 2.30-2.40 (1H, m), 2.51-2.61 (1H, m), 3.76-3.83 (1H, m), 4.30 (1H, d, J=4.8 Hz), 4.42 (1H, d, J=18.4 Hz), 4.48-4.58 (1H, m), 4.59 (1H, d, J=8.0 Hz), 4.62 (1H, d, J=18.4 Hz), 4.85 (1H, d, J=5.2 Hz), 5.12 (1H, dd, J1=10.4 Hz, J2=3.6 Hz), 5.20-5.25 (2H, m), 6.04 (1H, bs), 6.27-6.31 (1H, m), 7.22 (1H, d, J=10.4 Hz)

Example 11

Figure 8:
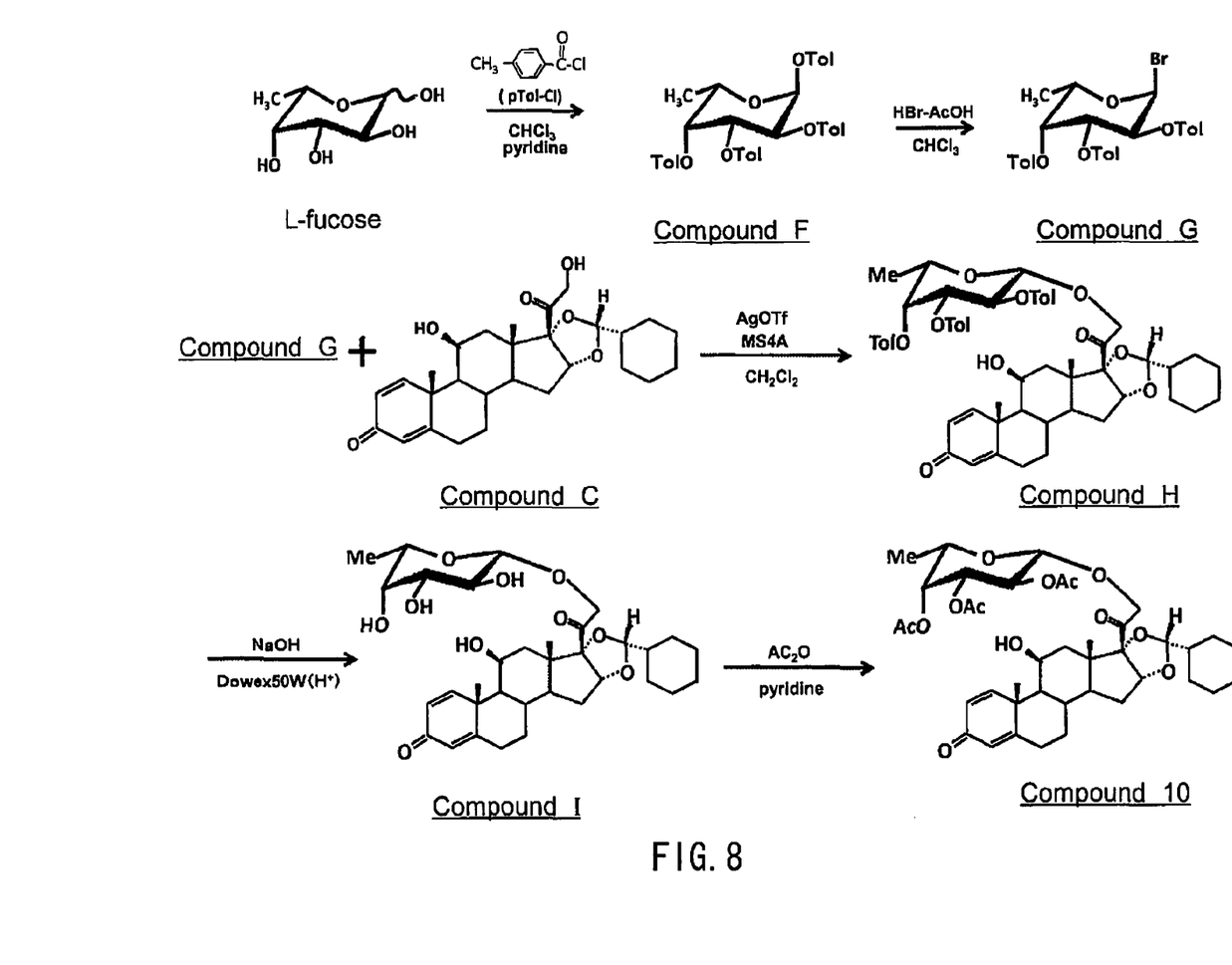
FIG. 8 is a reaction flow diagram for synthesis of Compound 10 from L-fucose (Example 10).

Synthesis of Compound 10 (FIG. 8)

Synthesis of Compound F: In chloroform (20 mL), L-fucose (1 g) was dissolved, and toluoylchloride (7 mL) and pyridine (4.5 mL) was added thereto, followed by stirring the mixture at room temperature for 12 hours, thereby carrying out the reaction. After the reaction solution was poured into ice water (200 mL) and after separation, the aqueous layer was extracted twice with chloroform (20 mL). The chloroform extract was washed sequentially with saturated copper sulfate solution (20 mL), saturated aqueous sodium hydrogen carbonate solution (20 mL) and saturated brine (20 mL), and dried over anhydrous magnesium sulfate. Then chloroform was evaporated under reduced pressure to obtain 3.9 g of compound F as white crystals.

Synthesis of Compound G: In anhydrous chloroform (20 mL), compound F (3.9 g) was dissolved, and 33% hydrogen bromide-acetic acid solution (9 mL) was added thereto on ice. After stirring the mixture for 12 hours at room temperature, the reaction solution was poured into ice water (300 mL) and after stirring, the mixed solution was separated. The aqueous layer was extracted twice with chloroform (40 mL). After washing with saturated aqueous sodium hydrogen carbonate solution (30 mL), the chloroform layer was washed with saturated brine. After drying over anhydrous magnesium sulfate, the resultant was evaporated under reduced pressure to obtain 3.5 g of compound G as white powder.

Rf=0.61 (n-hexane:ethyl acetate=3:1)

Synthesis of Compound H: Compound G (631 mg) and compound C (255 mg) were dissolved in anhydrous dichloromethane (5 mL), and molecular sieves 4 Å (1.8 g) was added thereto. After stirring the mixture under an argon gas atmosphere at room temperature for 15 minutes, silver trifluoromethanesulfonate (209 mg) was added at 0° C., and the resulting mixture was stirred at room temperature for a day in the dark while slowly heating. After adding the reaction solution to saturated aqueous sodium hydrogen carbonate solution (20 mL) and after stirring, the obtained mixture was extracted twice with chloroform (30 mL). After washing with saturated brine (20 mL), the chloroform layer was dried over anhydrous magnesium sulfate (5 g), and the resultant was evaporated under reduced pressure. The residue was subjected to separation and purification by silica gel column chromatography to obtain 623 mg (61%) of compound H as white powder.

Synthesis of Compound I: In methanol-THF solution (1:1.2 mL), compound H (1.13 g) was dissolved, and 1N aqueous sodium hydroxide solution (0.2 mL) was added thereto. The obtained mixture was stirred at room temperature for 3 hours, thereby carrying out the reaction. Dowex50Wx8 ($H^+$), which was strongly acid cation-exchange resin, was added to the reaction solution in small portions to neutralize. After filtering with suction, the solution was evaporated under reduced pressure. The residue was subjected to separation and purification by silica gel column chromatography (n-hexane-ethyl acetate=1:1) to obtain 390 mg of compound I as white powder.

Synthesis of Compound 10: Compound I (390 mg) was dissolved by pyridine (20 mL), after adding dropwise anhydrous acetic acid (2 mL) in small portions at 0° C. to 5° C. and stirring for additional 12 hours, thereby carrying out the reaction. Methanol (10 mL) was added to stop the reaction, and the solvent was evaporated. The resultant was subjected to purification by silica gel column chromatography (chloroform-methanol=10:1, 5:1) to obtain 256 mg of compound 10 as white powder.

$^1$H NMR ($CDCl_3$) δ:0.88 (3H, s, 18-$CH_3$), 1.45 (3H, s, 19-$CH_3$), 4.42 and 4.49 (each 1H, d, J=17.3 Hz, 21-$CH_2$), 6.03 (1H, d, J=1.7 Hz, H4), 6.28 (1H, dd, J=1.7, 10.0 Hz, H2), 7.27 (1H, d, J=10.0 Hz, H1). L-fucose moiety; 2.00, 2.12, 2.18 (each 3H, s, OAc×3), 1.22 (3H, d, J=6.3 Hz, $CH_3$), 3.81 (1H, dq, J=6.3, 1.0 Hz, H5), 4.56 (1H, d, J=7.8 Hz, H1), 5.04 (1H, dd, J=3.2, 10.5 Hz, H3), 5.23 (1H, dd, J=8.1, 10.5 Hz, H2), 5.04 (1H, dd, J=3.4, 1.0 Hz, H4).

FAB-MS 743 $(M+H)^+$.

Example 12

Figure 9:
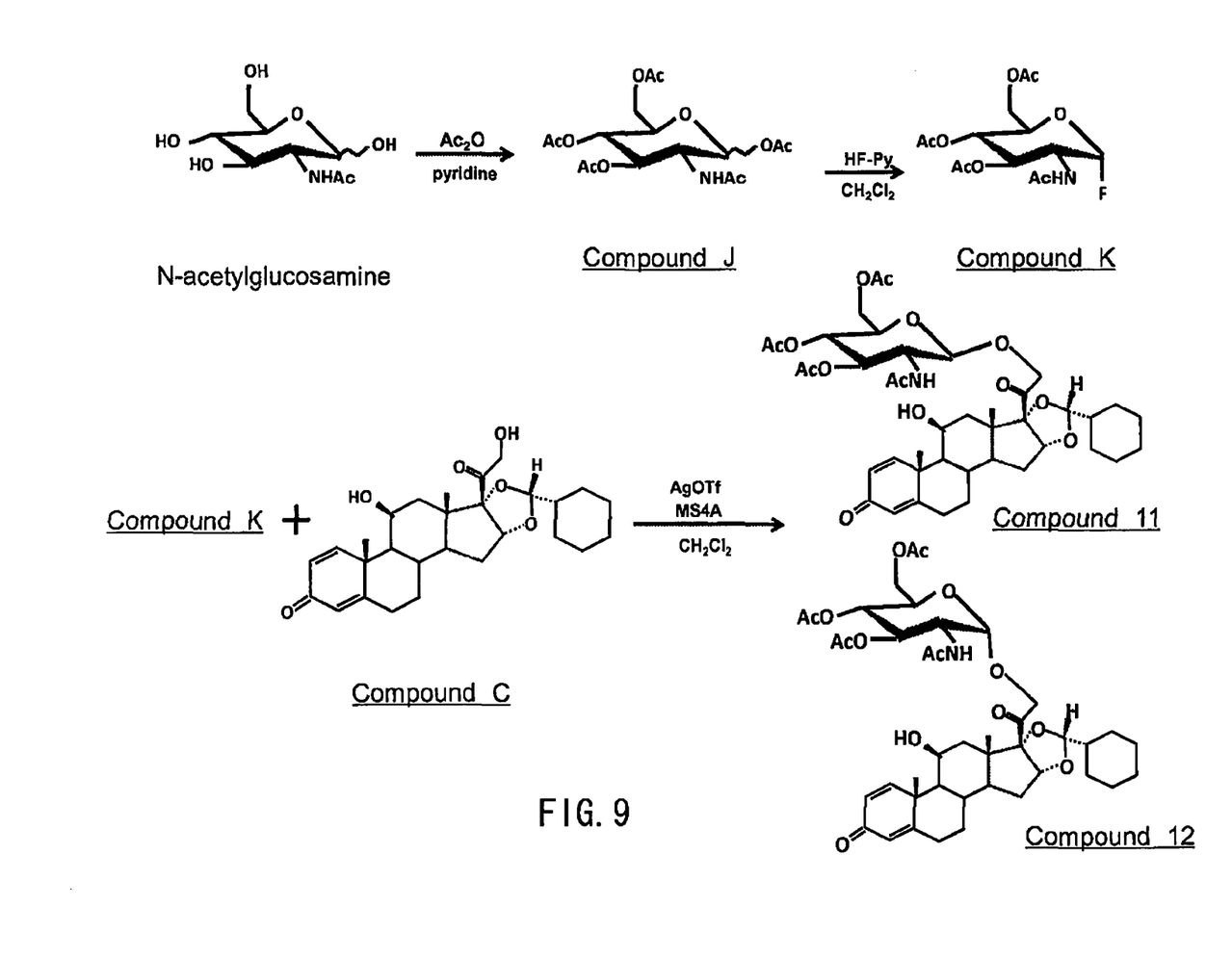
FIG. 9 is a reaction flow diagram for synthesis of Compound 11 and Compound 12 from N-acetylglucosamine (Example 11).

Synthesis of Compound 11 and Compound 12 (FIG. 9)

Synthesis of Compound J: In anhydrous acetic acid (5 mL) and pyridine (5 mL), N-acetylglucosamine (5.0 g) was dissolved, and the reaction was carried out at room temperature for 16 hours with stirring. The reaction solution was poured into ice water (300 mL) and after stirring, the mixture was extracted twice with chloroform (150 mL). After washing with saturated brine (50 mL), the resulting mixture was dried over anhydrous magnesium sulfate, and chloroform was evaporated under reduced pressure. Ether was added to the residue, the obtained solution was left to stand overnight in the refrigerator, thereby crystallizing. The crystals were filtered with suction to obtained 8.7 g of compound J as white powder.

Synthesis of Compound K: Compound J (1g) was dissolved in anhydrous dichloromethane (1 mL), and the resultant was added to 70% of hydrogen fluoride-pyridine (3 mL) in a plastic container cooled in an ice-bath, and the resulting mixture was stirred for a day while slowly returning the temperature to room temperature, thereby carrying out the reaction. After adding the reaction solution to ice-potassium fluoride aqueous (200 mL) and stirring for an hour, the obtained mixture was extracted twice with chloroform (40 mL). After sequentially washing with saturated copper sulfate solution, saturated aqueous sodium hydrogen carbonate solution and saturated brine, the resultant was dried over anhydrous magnesium sulfate, and chloroform was evaporated under reduced pressure. The residue was subjected to separation and purification by silica gel column chromatography (n-hexane-ethyl acetate=1:1, 1:2) to obtain 458 mg (51%) of compound K as white powder.

Rf=0.40 (n-hexane:ethyl acetate=1:2)

$^1$H NMR ($CDCl_3$) δ:2.001, 2.051, 2.053, 2.111 (each 3H, s, Ac×4), 4.15 (1H, m, H5), 4.16 (1H, dd, J=2.2, 12.7 Hz, H6a), 4.28 (1H, dd, J=4.3, 12.7 Hz, H6b), 4.40 (1H, m, H2), 5.22 (1H, t, J=8.1, 9.4 Hz, H4), 5.25 (1H, t, J=8.8, 9.6 Hz, H3), 5.65 (1H, dd, J=2.8, 52.6 Hz, H1), 6.08 (1H, d, J=9.0 Hz, NH).

FAB-MS 350 $(M+H)^+$.

Synthesis of Compound 11 and Compound 12: Compound K (242 mg) and Compound C (271 mg) were dissolved in anhydrous dichloromethane (4 mL), and molecular sieves 4 Å (300 mg) was added thereto. After stirring the mixture under an argon atmosphere at room temperature for 30 minutes, boron trifluoride ether complex (270 mL) was added dropwise dividedly in two times while cooling in an ice-salt bath. The mixture was stirred overnight at room temperature, thereby carrying out the reaction. The reaction was stopped by adding saturated aqueous sodium hydrogen carbonate solution (20 mL) and after filtering through Celite, the obtained filtrate was extracted three times with chloroform (10 mL). After washing with saturated brine (15 mL), the chloroform extract was dried over anhydrous magnesium sulfate, and the resultant was evaporated under reduced pressure. The residue was subjected to separation and purification by silica gel column chromatography (n-hexane-ethyl acetate=1:1, 1:2) to obtain compound 11 (116 mg, 25.1%) and compound 12 (139 mg, 30.1%) as white powder, respectively.

Compound 11

Rf=0.15 (n-hexane:ethyl acetate=1:2)

$^1$H NMR ($CDCl_3$) δ:0.89 (3H, s, 18-$CH_3$), 1.47 (3H, s, 19-$CH_3$), 6.03 (1H, d, J=1.8 Hz, H4), 6.29 (1H, dd, J=1.8, 8.3 Hz, H2), 7.28 (1H, d, J=8.3 Hz, H1). N-acetylglucosamine moiety; 1.988, 2.045, 2.046, 2.123 (each 3H, s, OAc×3, NHAc), 3.60 (1H, ddd, J=3.9, 4.2, 9.5 Hz, H5), 4.03 (1H, m, H2), 4.26 (1H, dd, J=12.1, 4.2 Hz, H6a), 4.31 (1H, dd, J=12.1, 3.9 Hz, H6b), 4.76 (1H, d, J=8.3 Hz, H1), 5.11 (1H, t, J=9.5, 9.3 Hz, H4), 5.16 (1H, t, J=9.5, 9.3 Hz, H3), 5.77 (3H, d, J=8.8 Hz, NH).

FAB-MS 800 $(M+H)^+$.

Compound 12

Rf=0.23 (n-hexane:ethyl acetate=1:2).

$^1$H NMR ($CDCl_3$) δ:0.94 (3H, s, 18-$CH_3$), 1.47 (3H, s, 19-$CH_3$), 6.03 (1H, d, J=1.5 Hz, H4), 6.29 (1H, dd, J=2.0, 10.0 Hz, H2), 7.28 (1H, d, J=10.0 Hz, H1). N-acetylglucosamine moiety; 1.988, 2.045, 2.046, 2.123 (each 3H, s, OAc×3, NHAc), 4.05 (1H, ddd, J=3.9, 4.2, 9.5 Hz, H5), 4.38 (1H, m, H2), 4.18 (1H, dd, J=12.1, 4.2 Hz, H6a), 4.26 (1H, dd, J=12.1, 3.9 Hz, H6b), 4.77 (1H, d, J=3.7 Hz, H1), 5.16 (1H, t, J=9.7 Hz, H4), 5.30 (1H, t, J=9.7 Hz, H3), 6.44 (3H, d, J=9.3 Hz, NH). FAB-MS 800 $(M+H)^+$.

Evaluation of Pharmacological Action

[Test for Croton Oil-Induced Ear Edema]

Croton oil ear edema test, which is a representative model for dermatitis, was used to study the pharmacological effect of compounds of the present invention.

(1) Experimental Method

Five individuals/group of rats of 5 weeks old (body weight, 128 g to 169 g) were used. One day before the test, the thickness of the right ear was measured under ether anesthesia using a dial thickness gauge, to obtain the Pre value. On the day of the test, 20 mg each of the ointments to be tested, which had been prepared to have various concentrations in white vaseline, was applied to the right auricle (both sides) of each rat, and a collar was then placed around the neck of the rat to prevent contacting/scratching and removal of the drug. Two hours later, the ointment was wiped off under ether anesthesia using absorbent cotton, and 0.1 mL of 5% croton oil (croton oil:ether:pyridine:distilled water=1:14:4:1) solution was applied dropwise to the both sides of the auricle while drying the solution with a drier (air blow), to induce ear edema. Six and 24 hours after the induction of the edema, the thickness of the right auricle was measured under ether anesthesia, and the edema rate and the edema suppression rate were calculated according to the equations below, which suppression rate is shown in Table 1.

Edema rate (%) = [Equation 1]

$$\frac{\text{Thickness of right ear} - Pre \text{ value}}{Pre \text{ value}} \times 100$$

Edema suppression rate (%) =

$$\left(1 - \frac{\left(\begin{array}{c}\text{Average edema rate of test drug-}\\ \text{applied group (\%)}\end{array}\right)}{\text{Average edema rate of control group (\%)}}\right) \times 100$$

(2) Results

The value increases as the pharmacological effect (anti-inflammatory effect) becomes stronger. The compounds of the present invention showed strong anti-inflammatory effects, and the effects were stronger than those of budesonide and ciclesonide, which are known steroid drugs. Unexpectedly, stronger effects than that of ciclesonide, which is the active main body compound, were observed. On the other hand, the compounds (control compounds 1 and 2) described in the 21-substituted glycosyl steroid compounds (WO 99/47541, WO 99/47542) did not show stronger effects than that of budesonide, and hence stronger effects than that of the active main body budesonide could not be obtained, while the compounds of the present invention showed strong anti-inflammatory effects which are higher than that of the active main body compound.

From these results, it was revealed that the compounds of the present invention show strong anti-inflammatory effects in the dermatitis model.

[Test for Croton Oil-Induced Granuloma]

Using the croton oil granuloma test, which is a test method with which the local anti-inflammatory action and the systemic side effect can be evaluated at the same time, the pharmacological effect and the systemic side effect of the compounds of the present invention were studied.

(1) Experimental Method

Five individuals/group of male Wistar rats having body weights of 180 to 225 g were used, and hair on the back of these rats was shaved with a clipper under ether anesthesia, followed by preparing an air pouch by subcutaneous injection of 20 mL of air at the back. On the next day, 1 mL of cottonseed oil containing 1% croton oil was administered to the pouch. Each test drug was suspended in the croton oil-containing cottonseed oil before administration. Seven days later, blood was collected from abdominal aorta under ether anesthesia, and exudate in the pouch was collected and its fluid amount was measured. Further, the thymus was removed, and its weight was measured. The weight of the exudate and the weight of the thymus are shown in Table 2 as the suppression rate and the atrophy rate (%) with respect to those of the control group.

(2) Results

As an index of the pharmacological activity (anti-inflammatory effect), the suppression effect for exudate was measured, and, as an index of the systemic side effect, the atrophic effect for the thymus was measured. In terms of atrophy of the thymus, budesonide and ciclesonide, which are known steroid drugs, caused atrophy of not less than 20% with a dose of 0.1 mg/rat, and caused evident atrophy of not less than 80% with a dose of 1 mg/rat. Further, the control compounds caused atrophy of not less than 20% with a dose of 1 mg/rat. On the other hand, the compounds of the present invention did not cause atrophy of not less than 20%. Further, in terms of the exudate-suppressing effect, which is an index of the pharmacological effect, the compounds of the present invention showed strong anti-inflammatory actions which were weaker than the known steroid drugs but the same with or higher than the control compounds. For a pharmaceutical, the balance between the main effects and the systemic side effects is important. The compounds of the present invention showed stronger anti-inflammatory effects than the control compounds, and atrophy of the thymus, which is an index of the systemic side effect, was not observed, so that it was revealed that the compounds of the present invention are safe anti-inflammatory steroid drugs with less systemic side effects.

[Test for DNCB-Induced Dermatitis]

The DNCB-induced dermatitis test, which is a representative model for allergic dermatitis, was used to study the pharmacological effect of the compound of the present invention.

(1) Experimental Method

Abdominal hair of rats (body weight, 205 to 230 g) under isoflurane anesthesia was shaved with an electric clipper and a shaver, and a test region having a size of 3 cm×4 cm was prepared, followed by applying 0.4 mL of 1% DNCB/acetone solution to the inside of the region, to carry out sensitization. Two weeks later, 1 mL of 1% DNCB/acetone solution was applied to the inside of the region to cause induction, and 4 days thereafter, reinduction was carried out. Two days after the reinduction, the skin was removed from the test region, and 5 predetermined positions were punched out using a punch having a diameter of 12 mm, followed by measuring the skin thickness using a dial thickness gauge. Further, to investigate the influence of side effects, the thymus was removed to measure its weight. Application of the test drug was carried out 4 hours after the first dermatitis induction such that 0.1 mL of the ointment is uniformly applied over the test region. Thereafter, the test drug was applied once per day, a total of 6 times until the next day of the reinduction (the day before removal of the skin). The skin thickness and the weight of the thymus are shown in Table 3 as the suppression rate and the atrophy rate (%) relative to those of the control group.

(2) Results

The skin thickness was measured as an index of the pharmacological activity (anti-inflammatory effect), and the atrophy effect for the thymus was measured as an index of the systemic side effects. By application of DNCB to an animal sensitized with DNCB, dermatitis is induced and the skin thickness increases. As the pharmacological activity (anti-inflammatory effect) increases, the skin thickness decreases. The compounds of the present invention showed stronger anti-inflammatory actions than those of 0.12% betamethasone valerate ointment and 0.05% betamethasone butyrate propionate ointment, which are used as therapeutic agents for dermatitis. Further, in terms of atrophy of the thymus, thymus atrophy of about 50% was observed with 0.12% betamethasone valerate ointment and 0.05% betamethasone butyrate propionate ointment, but no thymus atrophy was observed at all with the compounds of the present invention. For a pharmaceutical, the balance between the main effects and the systemic side effects is important. The compounds of the present invention showed stronger anti-inflammatory effects than the control compounds, and atrophy of the thymus, which is an index of the systemic side effect, was not observed, so that it was revealed that the compounds of the present invention are safe anti-inflammatory steroid drugs with less systemic side effects.

Based on comprehensive evaluation of the results of the croton oil-induced ear edema test, the croton oil-induced granuloma test and the DNCB-induced dermatitis test, it was revealed that the compounds of the present invention are safe anti-inflammatory steroid drugs having less systemic side effects and show strong effects especially by external administration.

[Amount of Production of Active Metabolite in Inflamed Skin and Non-Inflamed Skin]

The compounds of the present invention have the advantageous feature that they show the pharmacological effect after being metabolized to an active metabolite (des-ciclesonide) at the site of inflammation. The amount of the active metabolite produced when the compound of the present invention was applied to inflamed skin (skin whose dermatitis was induced by DNCB) or non-inflamed skin (normal skin) was compared.

(1) Experimental Method

Using, as the test region, an area of 3 cm×4 cm on the abdomen of a hairless rat of 9 weeks old, 0.4 mL of 1% DNCB/acetone solution was applied to the inside of the region under isoflurane anesthesia, to carry out sensitization. Two weeks later, 1 mL of 1% DNCB/acetone solution was applied to the inside of the region to cause induction, and, 48 hours thereafter, 0.1 mL of a test drug (0.1% ointment) was uniformly applied to the test region. The skin was removed 48 hours after the beginning of the application of the test drug. On the other hand, the test drug was also applied to a normal animal which had not been subjected to the sensitization and the induction, and the skin was removed 48 hours later. The skin was punched out using a punch having a diameter of 12 mm, and minced with scissors, followed by adding 50% acetonitrile in an amount of 5 mL per 1 g, and homogenizing the resultant with Polytron. After centrifugation (10,000 g, 4° C., 5 min.), the centrifugal supernatant was subjected to quantification of the amount of the active metabolite (des-ciclesonide) using LC/MS/MS. The amount of the active metabolite in the skin was converted to the amount of the drug per 1 g of the skin, which amount is shown in Table 4.

(2) Results

The compounds of the present invention were applied once to the inflamed skin or the non-inflamed skin, and the amount of the active metabolite was measured 48 hours later. As a result, in the inflamed skin, the amount of the active metabolite observed was about 10 times larger than that of the non-inflamed skin.

The compounds of the present invention have the feature that the compounds themselves do not have a steroid-like activity and are converted in vivo to active metabolites having a steroid-like activity. A usual steroid ointment shows similar extents of pharmacological effects (anti-inflammatory action, cytostatic action, immunosuppressive action and the like) in inflamed skin and non-inflamed skin. However, it was shown that the compounds of the present invention show different amounts of the metabolite between non-inflamed skin and inflamed skin, and, in inflamed skin, where the anti-inflammatory effect is expected, the amount of the active metabolite is larger and the anti-inflammatory effect is obtained, while in non-inflamed skin (normal skin), where the anti-inflammatory effect is not necessary, the amount of the active metabolite is smaller, so that the local side effects are less severe. From these facts, it was revealed that the compounds of the present invention have the advantageous feature that local side effects are reduced by adjustment of the amount of the active metabolite depending on the presence/absence of inflammation of the skin.

TABLE 1

| Test compound | Edema suppression rate of 6 hours after administration of inflammatory agent (%) Concentration of administered ointment (%) | | | | Edema suppression rate of 24 hours after administration of inflammatory agent (%) Concentration of administered ointment (%) | | | |
| --- | --- | --- | --- | --- | --- | --- | --- | --- |
| | 0 | 0.001 | 0.01 | 0.1 | 0 | 0.001 | 0.01 | 0.1 |
| Vaseline | 6.3 | — | — | — | 5.6 | — | — | — |
| Compound 3 | — | 50.3 | 46.1 | 51.7 | — | 48.1 | 58.0 | 56.0 |
| Compound 2 | — | 13.5 | 36.8 | 50.2 | — | 12.5 | 38.2 | 49.5 |
| Compound 4 | — | 30.8 | 46.3 | 54.4 | — | 33.8 | 70.2 | 71.7 |
| Compound 5 | — | 21.7 | 61.5 | 57.6 | — | 11.1 | 48.1 | 52.3 |
| Compound 6 | — | 27.5 | 53.1 | 53.1 | — | 30.5 | 45.8 | 55.1 |
| Compound 7 | — | 42.3 | 49.7 | 48.5 | — | 52.0 | 53.4 | 53.5 |
| Compound 8 | — | 24.2 | 36.0 | 33.4 | — | 25.9 | 40.1 | 49.6 |
| Compound 9 | — | 24.6 | 36.7 | 23.0 | — | 17.8 | 8.6 | 21.6 |
| Compound 10 | — | 42.4 | 55.9 | 38.9 | — | 45.8 | 33.2 | 39.9 |
| Compound 11 | — | 24.5 | 19.0 | 33.6 | — | 39.4 | 26.5 | 48.0 |
| Compound 12 | — | 29.9 | 16.7 | 12.4 | — | 36.6 | 29.6 | 9.1 |
| Budesonide | — | 11.8 | 32.3 | 48.1 | — | 7.6 | 33.5 | 45.1 |
| Ciclesonide | — | 9.1 | 30.3 | 49.4 | — | 9.4 | 24.5 | 43.5 |
| Control compound 1 | — | 4.3 | 13.8 | 20.0 | — | 4.7 | 8.4 | 24.2 |
| Control compound 2 | — | 0.0 | 6.4 | 23.3 | — | 0.0 | 1.8 | 11.4 |

TABLE 2

| Test compound | Rate of exudates suppression (pharmacological effects) Dose of test compound (mg/rat) | | | | Rate of thymus atrophy (systemic side effects) Dose of test compound (mg/rat) | | | |
| --- | --- | --- | --- | --- | --- | --- | --- | --- |
| | 0.001 | 0.01 | 0.1 | 1 | 0.001 | 0.01 | 0.1 | 1 |
| Compound 3 | 7.9 | 41.6 | 92.7 | 96.3 | 0.0 | 0.0 | 0.0 | 2.4 |
| Compound 4 | 17.9 | 44.5 | 87.0 | 94.5 | 0.0 | 0.0 | 0.0 | 0.0 |
| Compound 5 | 17.8 | 14.3 | 40.4 | 91.4 | 0.0 | 0.0 | 0.0 | 0.0 |
| Compound 6 | 0.0 | 12.0 | 31.2 | 71.9 | 0.0 | 0.0 | 0.0 | 0.0 |
| Compound 7 | 8.7 | 52.4 | 59.4 | 76.8 | 2.9 | 0.0 | 5.8 | 19.5 |
| Compound 8 | 19.1 | 42.1 | 78.0 | 95.0 | 0.0 | 0.0 | 0.0 | 0.5 |
| Compound 9 | 10.4 | 7.3 | 26.1 | 58.2 | 12.2 | 10.8 | 9.4 | 15.5 |
| Compound 10 | 4.6 | 0.0 | 4.8 | 5.3 | 0.0 | 0.0 | 0.0 | 0.0 |
| Compound 11 | 13.1 | 21.2 | 66.0 | 93.4 | 3.9 | 7.9 | 10.8 | 16.0 |
| Compound 12 | 3.6 | 0.0 | 0.0 | 76.5 | 0.0 | 5.8 | 17.7 | 8.0 |
| Budesonide | 10.8 | 66.9 | 91.6 | 94.3 | 7.3 | 17.7 | 74.5 | 87.5 |
| Budesonide(R) | 7.6 | 44.9 | 88.4 | 93.0 | 15.6 | 25.8 | 74.5 | 90.2 |
| Ciclesonide | 62.8 | 93.5 | 93.0 | 92.6 | 6.0 | 13.0 | 23.6 | 84.4 |
| desCIC | 62.0 | 74.1 | 92.7 | 94.1 | 0.0 | 11.7 | 22.4 | 86.4 |
| Control compound 1 | 0.0 | 19.5 | 91.3 | 96.2 | 7.3 | 9.3 | 12.3 | 40.0 |
| Control compound 2 | 0.0 | 29.3 | 93.3 | 94.4 | 9.7 | 14.3 | 15.8 | 27.0 |

TABLE 3

[Test for DNCB-induced Dermatitis]

| Test compound | Drug concentration | Rate of Skin thickness suppression (pharmacological effects) (%) | Rate of thymus atrophy (systemic side effects) (%) |
| --- | --- | --- | --- |
| Compound 3 | 0.01% | 46.1 | 0.0 |
| Compound 3 | 0.10% | 60.5 | 0.0 |
| Rinderon V ointment | 0.12% | 40.8 | 50.9 |
| Antebate ointment | 0.05% | 46.1 | 49.1 |

TABLE 4

[Amount of Production of Active Metabolite in Inflamed Skin and Non-inflamed Skin]

| Skin | Drug concentration of active metabolite (Compound C), 48 hours after test drug (Compound 3) were applied once |
|---|---|
| Non-inflamed skin (normal skin) | 119 ± 48 (ng/g) |
| DNCB-induced Dermatitis | 1272 ± 276 (ng/g) |

Mean ± S.D.

The invention claimed is:

1. A steroid compound of the Formula (1):

(1)

[wherein $R_1$ represents a group selected from the group consisting of H, $CH_3$, $C_2H_5$, $C_3H_7$ and $CH(CH_3)_2$, $R_2$ represents a group selected from $NH_2$, NHAc and $OCOR_1$, $R_3$ represents a group selected from the group consisting of $CH_3$, $COOCH_3$ and $CH_2OCOR_1$].

2. The compound according to claim 1, wherein $R_2$ is $OCOR_1$ and $R_3$ is $CH_2OCOR_1$.

3. The compound according to claim 1 or 2, wherein $R_1$ is $CH_3$.

4. The compound according to claim 1 or 2, wherein said $R_1$ is H.

5. The compound according to claim 1 or 2, wherein said $R_1$ is $C_2H_5$.

6. An anti-inflammatory composition comprising as an effective ingredient the compound according to any one of claims 1 to 2.

7. The anti-inflammatory composition according to claim 6, which is an external preparation.

8. The anti-inflammatory composition according to claim 7, which is a therapeutic agent for asthma to be administered by inhalation, a therapeutic agent for allergic rhinitis to be administered by intranasal administration, a therapeutic agent for arthritis or dermatitis to be administered by topical application, or a therapeutic agent for external ocular inflammatory diseases to be administered by instillation.

9. An arthritis therapeutic composition, comprising as an effective ingredient the compound according to any one of claims 1 to 2.

10. A therapeutic composition for ulcerative colitis, comprising as an effective ingredient the compound according to any one of claims 1 to 2.

* * * * *